(12) United States Patent
Okada et al.

(10) Patent No.: US 7,939,682 B2
(45) Date of Patent: May 10, 2011

(54) FLUORINE-CONTAINING ADAMANTANE DERIVATIVE, FLUORINE-CONTAINING ADAMANTANE DERIVATIVE HAVING POLYMERIZABLE GROUP, AND RESIN COMPOSITION CONTAINING SAME

(75) Inventors: Yasunari Okada, Chiba (JP); Hideki Yamane, Chiba (JP); Nobuaki Matsumoto, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 497 days.

(21) Appl. No.: 12/063,685

(22) PCT Filed: Aug. 11, 2006

(86) PCT No.: PCT/JP2006/315963
§ 371 (c)(1),
(2), (4) Date: Feb. 13, 2008

(87) PCT Pub. No.: WO2007/020901
PCT Pub. Date: Feb. 22, 2007

(65) Prior Publication Data
US 2009/0149665 A1    Jun. 11, 2009

(30) Foreign Application Priority Data
Aug. 17, 2005   (JP) ................................. 2005-236577

(51) Int. Cl.
*C07D 493/00*    (2006.01)
(52) U.S. Cl. ....................................... 549/510; 549/511
(58) Field of Classification Search ................... 549/510, 549/511
See application file for complete search history.

(56) References Cited

U.S. PATENT DOCUMENTS

| | | | |
|---|---|---|---|
| 6,066,711 A | 5/2000 | Hanazawa et al. | |
| 6,376,572 B1 | 4/2002 | Turri | |

FOREIGN PATENT DOCUMENTS

| | | |
|---|---|---|
| JP | 4 39665 | 2/1992 |
| JP | 6 305044 | 11/1994 |
| JP | 9 302077 | 11/1997 |
| JP | 11 2702 | 1/1999 |
| JP | 2001 048943 | 2/2001 |
| JP | 2002 182046 | 6/2002 |
| JP | 2003 212823 | 7/2003 |
| JP | 2005 008527 | 1/2005 |
| JP | 2005 23066 | 1/2005 |
| JP | 2005 146253 | 6/2005 |

*Primary Examiner* — Janet L. Andres
*Assistant Examiner* — Raymond Covington
(74) *Attorney, Agent, or Firm* — Oblon, Spivak, McClelland, Maier & Neustadt, L.L.P.

(57) ABSTRACT

Provided are a polymerizable group-containing and fluorine-containing adamantane derivative capable of affording a cured product having good heat resistance, good mechanical properties such as surface hardness and a low refractive index, a resin composition containing such a polymerizable group-containing adamantane derivative, and a fluorine-containing adamantane derivative which is useful as a reaction intermediate used for the production of the polymerizable group-containing and fluorine-containing adamantane derivative. Specifically provided are a fluorine-containing adamantane derivative represented by the general formula (I) below, a polymerizable group-containing and fluorine-containing adamantane derivative represented by the general formula (II) below, and a resin composition containing such a polymerizable group-containing and fluorine-containing adamantane derivative. In the formulas, $X^1$ and $X^2$ each represent OH or $NH_2$, a, b and c each represent an integer of 0 or more and $a+b+c \geq 1$, for example $a=b=0$ and $c=1$, $Z^3$ represents, for example, $-C_2H_4-$, s and t each represent an integer of 1 to 15, u represents an integer of 0 to 14, $s+t+u=16$, for example $s=2$, $t=14$, $u=0$, and $X^3$ represents, for example, $-O-CO-CH=CH_2$.

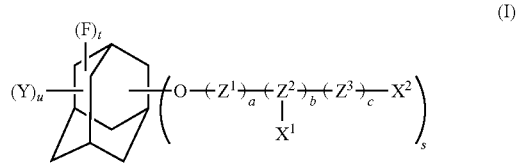

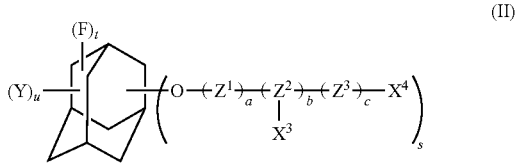

7 Claims, No Drawings

FLUORINE-CONTAINING ADAMANTANE DERIVATIVE, FLUORINE-CONTAINING ADAMANTANE DERIVATIVE HAVING POLYMERIZABLE GROUP, AND RESIN COMPOSITION CONTAINING SAME

TECHNICAL FIELD

The present invention relates to a novel fluorine-containing adamantane derivative, a polymerizable group-containing adamantane derivative, a method for preparing same, and a resin composition containing the polymerizable group-containing adamantane derivative. More specifically, the present invention is directed to a polymerizable group-containing and fluorine-containing adamantane derivative which is capable of giving a cured product having good heat resistance and good mechanical properties such as surface hardness and having a low refractive index, and which may be used as a reflection preventing film material for a display such as a liquid crystal or an organic EL element, a reflection preventing film material for a semiconductor resist, a refractive index modulation material for a volume hologram, and materials for optical fibers, optical waveguides and various types of lenses, to a resin composition containing same, to a fluorine-containing adamantane derivative useful as an intermediate material used for producing such a polymerizable group-containing and fluorine-containing adamantane derivative, and to a method capable of producing such a polymerizable group-containing and fluorine-containing adamantane derivative in an efficient manner.

BACKGROUND ART

Adamantane is a stable, highly symmetrical compound in which four cyclohexane rings are condensed to form a cage-like structure. It is known that adamantane derivatives, which show peculiar functions, are useful as raw materials for medical materials and highly functional industrial materials. Further, because adamantane has specific optical characteristics and heat resistance, an attempt has been made to use it as, for example, an optical disc substrate, an optical fiber or a lens (see, for example, Patent Documents 1 and 2). An other attempt has also been made to use an adamantane ester as a raw material for a resin photoresist by utilizing its sensitivity to an acid, dry etching resistance and transparency to UV rays (see, for example, Patent Document 3).

In recent years, studies have been made to attain high fineness, wide sight angle and high image quality of flat panel displays using liquid crystals or organic electroluminescence (EL) elements, to use high frequency in electronic circuits and to achieve high performance and improvement of optical and electronic parts in optical circuits and optical communication.

In this circumstance, an attempt is being made to improve fluorine-containing material which is used in a low refraction index layer for a reflection preventing film of displays and in optical fibers and optical waveguides for optical communication. Since, in general, a fluorine atom-containing compound has a low refractive index, studies are being made to use a fluorine-containing resin material having a low refractive index for a reflection preventing film for liquid crystals and organic EL displays, a lens such as a Fresnel lens, a lenticular lens or a microlens array, an optical fiber and an optical waveguide.

For example, in a reflection preventing film in which low refractive index and high refractive index layers are alternately laminated for the prevention of reflection, a straight chain polymer of a fluorine-containing acrylate is used as a resin of the low refractive index layer (see, for example, Patent Documents 4 and 5). Because the resin is straight-chained, a sufficiently high surface hardness cannot be obtained and a problem is caused with respect to the mar resistance. In the field of optical fibers and optical waveguides, it is well known that C—H bonds in an organic compound cause an optical loss. To cope with this problem, a material in which such C—H bonds are substituted by C—F bonds is used. For example, the use of a straight chain fluorine-containing acrylate resin is proposed (see, for example, Patent Document 6). The heat resistance of such an acrylate resin, however, is insufficient to withstand reflow soldering and heat generation at the time of communication.

Patent Document 1: Japanese Unexamined Patent Application Publication No. H06-305044
Patent Document 2: Japanese Unexamined Patent Application Publication No. H09-302077
Patent Document 3: Japanese Unexamined Patent Application Publication No. H04-39665
Patent Document 4: Japanese Unexamined Patent Application Publication No. H11-2702
Patent Document 5: Japanese Unexamined Patent Application Publication No. 2001-48943
Patent Document 6: Japanese Unexamined Patent Application Publication No. 2002-182046

DISCLOSURE OF THE INVENTION

In view of the above circumstance, the present invention has as its object the provision of a polymerizable group-containing and fluorine-containing adamantane derivative which is capable of giving a cured product having good heat resistance and good mechanical properties such as surface hardness and showing a low refractive index, and which may be suitably used as a reflection preventing film material for a display such as an organic EL element or a liquid crystal, a reflection preventing film material for a semiconductor resist, a refractive index modulation material for a volume hologram, and materials for optical fibers, optical waveguides and various types of lenses; a resin composition containing same; and a fluorine-containing adamantane derivative useful as an intermediate material used for producing such a polymerizable group-containing and fluorine-containing adamantane derivative.

The present inventors have made an earnest study with a view toward fulfill the above object and, as a result, have found that a resin composition capable of affording a cured product having good heat resistance and good mechanical properties such as surface hardness and providing a low refractive index may be obtained by using a polymerizable group-containing and fluorine-containing adamantane derivative having a specific structure. It has been also found that a fluorine-containing adamantane derivative having a specific structure is useful as a reaction intermediate for the production of the above-described polymerizable group-containing and fluorine-containing adamantane derivative having a specific structure. The present invention has been completed on the basis of such findings.

Thus, the present invention provides a fluorine-containing adamantane derivative, a polymerizable group-containing and fluorine-containing adamantane derivative, a method for producing same and a resin composition containing same, as follows.

1. A fluorine-containing adamantane derivative represented by the following general formula (I).

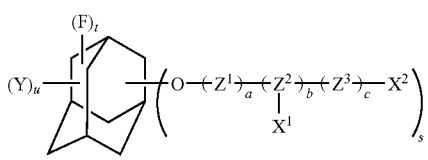
(I)

[wherein $Z^1$, $Z^2$ and $Z^3$ represent the groups represented by the following formulas:

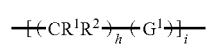
$Z^1$

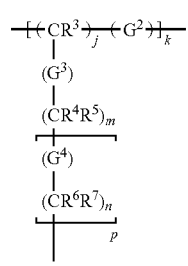
$Z^2$

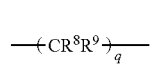
$Z^3$ (where $R^1$ to $R^9$ each independently represent a hydrogen atom, a halogen atom or an aliphatic hydrocarbon group which may contain a heteroatom or heteroatoms, $G^1$ to $G^4$ each independently represent a single bond or a heteroatom, h, i, j, k, n, p and q each represent an integer of 1 or more, and m represents an integer of 0 or more), a, b and c each represent an integer of 0 or more with the proviso that $a+b+c \geq 1$, $X^1$ and $X^2$ each independently represent a hydroxyl group or an amino group, Y represents a hydrogen atom, a hydrocarbon group, a halogenated hydrocarbon group, a cyclic hydrocarbon group, a halogenated cyclic hydrocarbon group, a hydroxyl group or a carboxyl group, or two Y's may be taken together to represent a =O group, s and t each represent an integer of 1 to 15 and u represents an integer of 0 to 14 with the proviso that $s+t+u=16$.]

2. A polymerizable group-containing and fluorine-containing adamantane derivative represented by the following general formula (II).

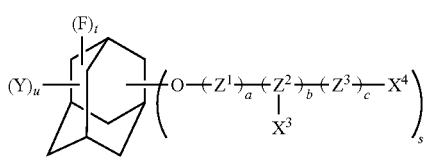
(II)

[wherein $Z^1$, $Z^2$, $Z^3$, Y, a, b, c, s, t and u are as defined above, $X^3$ and $X^4$ each independently represent a polymerizable group represented by any of the following general formulas (III) to (VI):

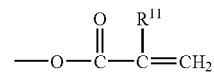
(III)

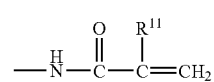
(IV)

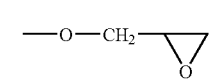
(V)

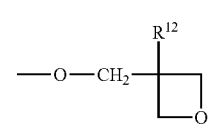
(VI)

(where $R^{11}$ represents a hydrogen atom, a methyl group or a trifluoromethyl group and $R^{12}$ represents a $C_1$ to $C_5$ hydrocarbon group)].

3. A process for producing a polymerizable group-containing and fluorine-containing adamantane derivative represented by the general formula (II) shown below, comprising reacting a fluorine containing adamantane derivative represented by the general formula (I) shown below with a compound having a polymerizable group.

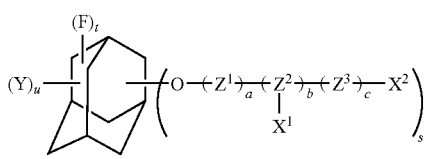
(I)

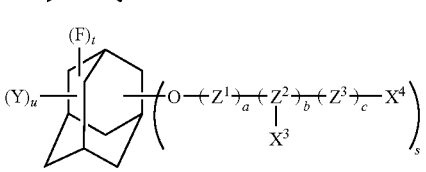
(II)

[wherein $Z^1$, $Z^2$, $Z^3$, $X^1$, $X^2$, $X^3$, $X^4$, Y, a, b, c, s, t and u are as defined above.]

4. A resin composition comprising a polymerizable group-containing and fluorine-containing adamantane derivative as recited in 2 above.

A polymerizable group-containing and fluorine-containing adamantane derivative and a resin composition containing the adamantane derivative according to the present invention are capable of giving a cured product which has good heat resistance and good mechanical properties such as surface hardness, which provides a low refractive index, and which may be suitably used as a reflection preventing film material for a display such as an organic EL element or a liquid crystal, a reflection preventing film material for a semiconductor resist, a refractive index modulation material for a volume hologram, and materials for optical fibers, optical waveguides and various types of lenses.

BEST MODE FOR CARRYING OUT THE INVENTION

The fluorine-containing adamantane derivative of the present invention (herein after occasionally referred to as "the fluorine-containing adamantane derivative (I)") is represented by the following general formula (I).

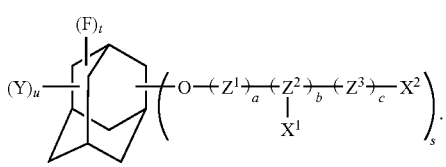

(I)

In the above formula, $Z^1$, $Z^2$ and $Z^3$ represent the groups shown below.

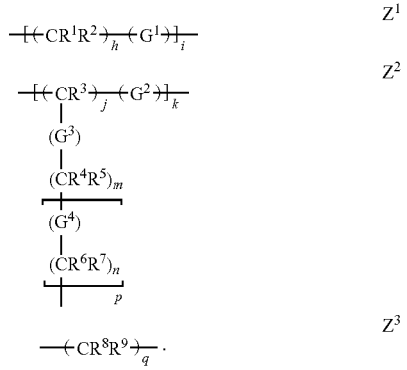

In the above formulas, $R^1$ to $R^9$ each independently represent a hydrogen atom, a halogen atom or an aliphatic hydrocarbon group which may contain a heteroatom or heteroatoms. As the aliphatic hydrocarbon group which may contain a heteroatom or heteroatoms, there may be mentioned, for example, a methoxy group, an ethoxy group, a butoxy group, a hydroxymethyl group, a hydroxyethyl group, a methylthio group, an ethylthio group, a methylamino group, a dimethylamino group, an ethylamino group and a diethylamino group. $G^1$ to $G^4$ each independently represent a single bond or a heteroatom. Examples of the heteroatom include a nitrogen atom, an oxygen atom and a sulfur atom. The symbols h, i, j, k, n, p and q are each an integer of 1 or more, while m is an integer of 0 or more.

In the general formula (I), a, b and c each represent an integer of 0 or more with the proviso that $a+b+c \geq 1$. $X^1$ and $X^2$ each independently represent a hydroxyl group or an amino group and Y represents a hydrogen atom, a hydrocarbon group, a halogenated hydrocarbon group, a cyclic hydrocarbon group, a halogenated cyclic hydrocarbon group, a hydroxyl group or a carboxyl group, or two Y's may be taken together to represent a =O group.

The hydrocarbon group represented by Y is preferably a $C_1$ to $C_{10}$ alkyl or alkoxy group. The alkyl group may be straight chained, branched or cyclic. Specific examples of the alkyl group include a methyl group, an ethyl group, a propyl group, a butyl group or a cyclohexyl group. As the alkoxy group, there may be mentioned, for example, a methoxy group and an ethoxy group. The halogenated hydrocarbon group may be, for example, a group obtained by substituting at least one of the hydrogen atoms of the above-described hydrocarbon group with a halogen atom or atoms, such as a trifluoromethyl group. The halogen atom may be, for example, fluorine, chlorine, bromine or iodine.

As the cyclic hydrocarbon group represented by Y, there may be mentioned, for example, a $C_5$ to $C_{10}$ cycloalkyl group such as a cylopentyl group, a methylcyclopentyl group, a cyclohexyl group, a methylcyclohexyl group and an ethylcyclohexyl group. The halogenated cyclic hydrocarbon group may be, for example, a group obtained by substituting at least one of the hydrogen atoms of the above-described cyclic hydrocarbon group with a halogen atom or atoms, such as a fluorocyclopentyl group, a fluorocyclohexyl group, a trifluoromethylcyclopentyl group or a trifluoromethylcyclohexyl group. The symbol s is an integer of 1 to 15, preferably 1 to 12, t is an integer of 1 to 15, preferably 4 to 15, and u is an integer of 0 to 14, preferably 0 to 4, with the proviso that s+t+u=16.

As the fluorine-containing adamantane derivative having the above general formula (I) in which $X^1$ and/or $X^2$ are each a hydroxyl group, there may be mentioned, for example, perfluoro-1-(2-hydroxyethoxy)adamantane, perfluoro-2-(2-hydroxyethoxy)adamantane, perfluoro-2-methyl-2-(2-hydroxyethoxy)adamantane, perfluoro-4-oxo-2-(2-hydroxyethoxy)adamantane, perfluoro-1,3-bis(2-hydroxyethoxy) adamantane, perfluoro-1,3,5-tris(2-hydroxyethoxy) adamantane, perfluoro-1,3,5,7-tetrakis(2-hydroxyethoxy) adamantane, perfluoro-1-(2-hydroxypropoxy)adamantane, perfluoro-2-(2-hydroxypropoxy)adamantane, perfluoro-2-methyl-2-(2-hydroxypropoxy)adamantane, perfluoro-4-oxo-2-(2-hydroxypropoxy)adamantane, perfluoro-1,3-bis(2-hydroxypropoxy)adamantane, perfluoro-1,3,5-tris(2-hydroxypropoxy)adamantane, perfluoro-1,3,5,7-tetrakis(2-hydroxypropoxy)adamantane, perfluoro-1-(2-hydroxybutoxy)adamantane, perfluoro-2-(2-hydroxybutoxy)adamantane, perfluoro-2-methyl-2-(2-hydroxybutoxy)adamantane, perfluoro-4-oxo-2-(2-hydroxybutoxy)adamantane, perfluoro-1,3-bis(2-hydroxybutoxy)adamantane, perfluoro-1,3,5-tris(2-hydroxybutoxy)-adamantane, perfluoro-1,3,5,7-tetrakis(2-hydroxybutoxy)adamantane, perfluoro-1-(2-hydroxypentyloxy)adamantane, perfluoro-2-(2-hydroxypentyloxy)adamantane, perfluoro-2-methyl-2-(2-hydroxypentyloxy)adamantane, perfluoro-4-oxo-2-(2-hydroxypentyloxy)adamantane, perfluoro-1,3-bis(2-hydroxypentyloxy)adamantane, perfluoro-1,3,5-tris(2-hydroxypentyloxy)-adamantane, perfluoro-1,3,5,7-tetrakis (2-hydroxypentyloxy)adamantane, perfluoro-1-[(2-hydroxyethoxy) ethoxy]-adamantane, perfluoro-2-[(2-hydroxyethoxy) ethoxy]adamantane, perfluoro-2-methyl-2-[(2-hydroxyethoxy) ethoxy]adamantane, perfluoro-4-oxo-2-[(2-hydroxyethoxy) ethoxy]adamantane, perfluoro-1,3-bis [(2-hydroxyethoxy) ethoxy]adamantane, perfluoro-1,3,5-tris [(2-hydroxybutoxy)adamantane, perfluoro-1,3,5,7-tetrakis [(2-hydroxyethoxy) ethoxy]adamantane, perfluoro-1-(2,3-dihydroxypropoxy)adamantane, perfluoro-2-(2,3-dihydroxypropoxy)adamantane, perfluoro-2-methyl-2-(2,3-dihydroxypropoxy)adamantane, perfluoro-4-oxo-2-(2,3-dihydroxypropoxy)adamantane, perfluoro-1,3-bis(2,3-dihydroxypropoxy)adamantane, perfluoro-1,3,5-tris(2,3-dihydroxypropoxy)adamantane and perfluoro-1,3,5,7-tetrakis(2,3-dihydroxypropoxy)adamantane.

As the fluorine-containing adamantane derivative having the above general formula (I) in which $X^1$ and/or $X^2$ are each an amino group, there may be mentioned, for example, perfluoro-1-(2-aminoethoxy)adamantane, perfluoro-2-(2-aminoethoxy)adamantane, perfluoro-2-methyl-2-(2-aminoethoxy)adamantane, perfluoro-4-oxo-2-(2-aminoethoxy) adamantane, perfluoro-1,3-bis(2-aminoethoxy)adamantane, perfluoro-1,3,5-tris(2-aminoethoxy)adamantane, perfluoro-1,3,5,7-tetrakis(2-aminoethoxy)adamantane, perfluoro-1-(2-aminopropoxy)adamantane, perfluoro-2-(2-amino-propoxy) adamantane, perfluoro-2-methyl-2-(2-aminopropoxy) adamantane, perfluoro-4-oxo-2-(2-aminopropoxy) adamantane, perfluoro-1,3-bis(2-aminopropoxy) adamantane, perfluoro-1,3,5-tris(2-aminopropoxy)

adamantane, perfluoro-1,3,5,7-tetrakis(2-aminopropoxy) adamantane, perfluoro-1-(2-aminobutoxy)adamantane, perfluoro-2-(2-aminobutoxy)adamantane, perfluoro-2-methyl-2-(2-aminobutoxy)adamantane, perfluoro-4-oxo-2-(2-aminobutoxy)adamantane, perfluoro-1,3-bis(2-aminobutoxy)adamantane, perfluoro-1,3,5-tris(2-aminobutoxy) adamantane and perfluoro-1,3,5,7-tetrakis(2-aminobutoxy) adamantane.

As the fluorine-containing adamantane derivative having the above general formula (I) in which $X^1$ and/or $X^2$ are hydroxyl and amino groups, there may be mentioned, for example, perfluoro-1-(2-hydroxyethoxy)-3-(2-aminoethoxy)adamantane, perfluoro-1,3-bis(2-hydroxyethoxy)-5-(2-aminoethoxy)adamantane, perfluoro-1,3-bis(2-hydroxyethoxy)-5,7-bis(2-aminoethoxy)adamantane, perfluoro-1 (2-hydroxypropoxy)-3-(2-aminopropoxy)adamantane, perfluoro-1,3-bis(2-hydroxypropoxy)-5-(2-aminopropoxy)adamantane, perfluoro-1,3-bis(2-hydroxypropoxy)-5,7-bis(2-aminopropoxy)adamantane, perfluoro-1 (2-hydroxybutoxy)-3-(2-aminobutoxy)adamantane, perfluoro-1,3-bis(2-hydroxybutoxy)-5-(2-aminobutoxy)adamantane, and perfluoro-1,3-bis(2-hydroxybutoxy)-5,7-bis(2-aminobutoxy)adamantane.

The fluorine-containing adamantane derivative (I) may be prepared by etherification of a hydroxyl group-containing and fluorine-containing adamantane with a halogen-containing compound. As the fluorine-containing adamantane having a hydroxyl group, there may be mentioned, for example, perfluoro-1-adamantanol, perfluoro-2-adamantanol, perfluoro-2-methyl-2-adamantanol, perfluoro-4-oxo-2-adamantanol, perfluoro-1,3-adamantane diol, perfluoro-1,3,5-adamantane triol and pentafluoro-1,3,5,7-adamantane tetraol.

As the halogen-containing compound to be reacted with the above hydroxyl group-containing and fluorine-containing adamantane, there may be mentioned, for example, 2-chloroethanol, 2-bromoethanol, 3-chloro 1-propanol, 3-bromo-1-propanol, 1-chloro-2-propanol, 1-bromo-2-propanol, 2-chloro-1-propanol, 2-bromo-1-propanol, 4-chloro-1-butanol, 4-bromo-1-butanol, 5-chloro-1-pentanol, 5-bromo-1-pentanol, 2-(2-chloroethoxy) ethanol, 2-[2-(2-chloroethoxy) ethoxy]ethanol, 3-chloro-1,2-propane diol, 2-chloroethylamine, 2-bromoethylamine, 3-chloropropylamine, 3-bromopropylamine, 4-chlorobutylamine and 4-bromobutylamine.

The reaction of the above-described hydroxyl group-containing and fluorine-containing adamantane with the above-described halogen-containing compound is generally carried out at a temperature of 0 to 200° C., preferably 50 to 150° C. A reaction temperature of 0° C. or higher can reduce the reaction time because the reaction rate is not lowered and is appropriate. When the reaction temperature is not higher than 200° C., the product can be prevented from coloring. The reaction pressure in terms of absolute pressure is 0.01 to 10 MPa, preferably between ambient pressure and 1 MPa. When the pressure is 10 MPa or less, it is not necessary to use specific apparatuses because safety is ensured. This is industrially advantageous. The reaction time is generally about 1 minute to 24 hours, preferably 1 to 10 hours.

In performing the above reaction, it is preferable to use potassium iodide as a catalyst because the reaction rate is enhanced. The proportion of potassium iodide relative to the reaction raw material is such that the molar ratio of the hydroxyl group-containing and fluorine-containing adamantine to the potassium iodide falls within the range of 0.1 to 5, preferably 0.5 to 2.

The reaction is carried out in the absence or presence of a solvent. It is advantageous that the solvent used can dissolve at least 0.5% by mass, preferably at least 5% by mass, of the above-described hydroxyl group-containing and fluorine-containing adamantane. The solvent may be used in such an amount as to provide a concentration of the above-described fluorine-containing adamantane of at least 0.5% by mass, preferably at least 5% by mass. The above-described fluorine-containing adamantane may be present in a suspended state but is preferably in a dissolved state. Specific examples of the solvent include hexane, heptane, toluene, DMF (dimethylformamide), NMP (N-methyl-2-pyrrolidone), DMAc (N,N-dimethylacetaminde), DMSO (dimethylsulfoxide), ethyl acetate, diethyl ether and tetra hydrofuran. These solvents may be used singly or in combination of two or more thereof. The above-described halogen-containing compound may be also used as the solvent.

The reaction product may be refined by distillation, crystallization, column separation, etc. The refining method may be suitably selected depending upon the properties of the product and the kind of impurities.

The polymerizable group-containing and fluorine-containing adamantane derivative (herein after also occasionally referred to as "fluorine-containing adamantane derivative (II)") is represented by the following general formula (II).

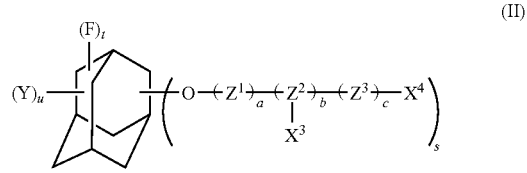

(II)

wherein $Z^1$, $Z^2$, $Z^3$, Y, a, b, c, s, t and u are as defined above, and $X^3$ and $X^4$ each independently represent a polymerizable group represented by any of the following general formulas (III) to (VI).

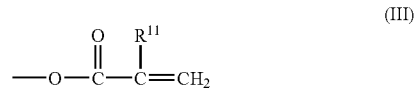

(III)

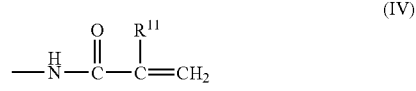

(IV)

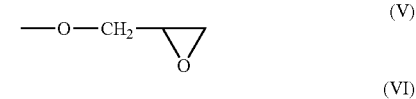

(V)

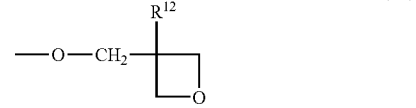

(VI)

In the above formulas, $R^{11}$ represents a hydrogen atom, a methyl group or a trifluoromethyl group and $R^{12}$ represents a $C_1$ to $C_5$ hydrocarbon group. As the $C_1$ to $C_5$ hydrocarbon group, there may be mentioned an alkyl group and an alkoxy group. The alkyl group may be straight chained, branched or cyclic. Specific examples of the alkyl group include a methyl group, an ethyl group, a propyl group and a butyl group. The alkoxy group may be, for example, a methoxy group or an ethoxy group.

The fluorine-containing adamantane (II) may be prepared by using the above-described fluorine-containing adamantane (I) as an intermediate. Thus, the intermediate is reacted with a polymerizable group-containing compound for conventional esterification, amidization or glycidyl etherification.

The polymerizable group-containing compound to be reacted with the above-described fluorine-containing adamantane (I) to form an ester or an amide may be, for example, acrylic acid, methacrylic acid, □-trifluoromethylacrylic acid, acrylic chloride, methacrylic chloride and □-trifluoromethylacrylic chloride.

A fluorine-containing adamantane ester derivative as the fluorine-containing adamantane derivative (II) may be prepared by a conventional azeotropic dehydration or acid chloride method. The azeotropic dehydration is generally carried out at a temperature of about 50 to 200° C., preferably 100 to 150° C. A reaction temperature of 50° C. or higher can reduce the reaction time because the reaction rate is not lowered and is appropriate. When the reaction temperature is not higher than 200° C., side reactions are prevented from occurring and, further, the product can be prevented from coloring. The reaction pressure in terms of absolute pressure is 0.01 to 10 MPa, preferably between ambient pressure and 1 MPa. When the pressure is 10 MPa or less, it is not necessary to use specific apparatuses because safety is ensured. This is industrially advantageous. The reaction time is generally about 1 minute to 24 hours, preferably 1 to 10 hours.

The above reaction is performed using a catalyst such as sulfuric acid or p-toluenesulfonic acid. The catalyst is used in an amount of 0.01 to 10 mol %, preferably 0.05 to 5 mol %, based on the fluorine-containing adamantane derivative (I).

The reaction is carried out in the absence or presence of a solvent. It is advantageous that the solvent used can dissolve at least 0.5% by mass, preferably at least 5% by mass, of the above-described fluorine-containing adamantane derivative (I). The solvent may be used in such an amount as to provide a concentration of the above-described fluorine-containing adamantane derivative (I) of at least 0.5% by mass, preferably at least 5% by mass. The above-described fluorine-containing adamantane derivative (I) may be present in a suspended state but is preferably in a dissolved state. Specific examples of the solvent include nonane, decane, undecane, cyclohexane, methylcyclohexane, toluene, xylene, DMF (dimethylformamide), NMP (N-methyl-2-pyrrolidone), DMAc (N, N-dimethylacetaminde) and DMSO (dimethylsulfoxide). These solvents may be used singly or in combination of two or more thereof.

In performing the above reaction, a polymerization inhibitor such as hydroquinone, methoquinone, phenothiazine or methoxyphenothiazine may be added, if necessary. Such a polymerization inhibitor may be generally used in an amount of about 10 to 10,000 ppm by mass, preferably 50 to 2,000 ppm by mass, based on the fluorine-containing adamantane derivative (I).

When a fluorine-containing adamantane ester derivative as the fluorine-containing adamantane derivative (II) is produced by an acid chloride method, the reaction is generally carried out at a temperature of about −50 to 100° C., preferably 0 to 50° C. A reaction temperature of −50° C. or higher can reduce the reaction time because the reaction rate is not lowered and is appropriate. When the reaction temperature is not higher than 100° C., side reactions are prevented from occurring and, further, the product can be prevented from coloring. The reaction pressure in terms of absolute pressure is 0.01 to 10 MPa, preferably between ambient pressure and 1 MPa. When the pressure is 10 MPa or less, it is not necessary to use specific apparatuses because safety is ensured. This is industrially advantageous. The reaction time is generally about 1 minute to 24 hours, preferably 1 to 10 hours.

In performing the above reaction, an organic amine, such as triethylamine, tributylamine, pyridine or dimethylaminopyridine, or an inorganic base, such as sodium hydroxide, potassium hydroxide, sodium carbonate, potassium carbonate, sodium phosphate or potassium phosphate, may be added as a scavenger for an acid formed in situ during the reaction. Such a base may be used in such an amount as to provide a molar ratio of the base to the fluorine-containing adamantane derivative (I) of about 0.5 to 5, preferably 1 to 3.

The reaction is carried out in the absence or presence of a solvent. It is advantageous that the solvent used can dissolve at least 0.5% by mass, preferably at least 5% by mass, of the above-described fluorine-containing adamantane derivative (I). The solvent may be used in such an amount as to provide a concentration of the above-described fluorine-containing adamantane derivative (I) of at least 0.5% by mass, preferably at least 5% by mass. The above-described fluorine-containing adamantane derivative (I) may be present in a suspended state but is preferably in a dissolved state. Specific examples of the solvent include hexane, heptanes, cyclohexane, toluene, DMF (dimethylformamide), NMP (N-methyl-2-pyrrolidone), DMAc (N, N-dimethylacetaminde), DMSO (dimethylsulfoxide), ethyl acetate, diethyl ether, tetra hydrofuran, dichloromethane and chloroform. These solvents may be used singly or in combination of two or more thereof.

In performing the above reaction, a polymerization inhibitor such as hydroquinone, methoquinone, phenothiazine or methoxyphenothiazine may be added, if necessary. Such a polymerization inhibitor may be generally used in an amount of about 10 to 10,000 ppm by mass, preferably 50 to 2,000 ppm by mass, based on the fluorine-containing adamantane derivative (I).

In either of the azeotropic dehydration method and the acid chloride method, the obtained reaction product may be refined by distillation, crystallization, column separation, etc. The refining method may be suitably selected depending upon the properties of the product and the kind of impurities.

A fluorine-containing adamantane amide derivative as the fluorine-containing adamantane derivative (II) may also be prepared under the same conditions as those for the production of the above-described fluorine-containing adamantane ester derivative. In this case, dicyclohexylcarbodiimide, carbonyldiimidazole or 1-hydroxybenzotriazole may be used as a condensation agent. Such a condensation agent is used in such an amount as to provide a molar ratio of the condensation agent to the fluorine-containing adamantane derivative (I) of about 1 to 10, preferably 1 to 5.

A fluorine-containing adamantane derivative having an epoxy group or an oxetanyl group may be prepared using the fluorine-containing adamantane derivative (I) as an intermediate. In this case, the compound to be reacted with the fluorine-containing adamantane derivative (I) may be, for example, epichlorohydrin, epibromohydrin, 3-chloromethyl-3-methyloxetane or 3-chloromethyl-3-ethyloxetane. The reaction of the above-described compound with the fluorine-containing adamantane derivative (I) is generally carried out at a temperature of about 0 to 200° C., preferably 50 to 150° C. A reaction temperature of 0° C. or higher can reduce the reaction time because the reaction rate is not lowered and is appropriate. When the reaction temperature is not higher than 200° C., the product can be prevented from coloring. The reaction pressure in terms of absolute pressure is 0.01 to 10 MPa, preferably between ambient pressure and 1 MPa. When the pressure is 10 MPa or less, it is not necessary to use specific apparatuses because safety is ensured. This is industrially advantageous. The reaction time is generally about 1 minute to 24 hours, preferably 1 to 10 hours.

The above reaction is generally carried out in the presence of a basic catalyst. As the basic catalyst, there may be mentioned, for example, sodium amide, triethylamine, tributylamine, trioctylamine, pyridine, N,N-dimethylaniline, 1,5-diazabicyclo[4.3.0]nonene-5 (DBN), 1,8-diazabicyclo[5.4.0]undecene-7 (DBU), tetramethylammonium chloride, tetraethylammonium chloride, sodium hydroxide, potassium hydroxide, sodium hydride, sodium phosphate or potassium phosphate, sodium carbonate, potassium carbonate, silver oxide, sodium methoxide or potassium t-butoxide.

Such a basic catalyst is used in such an amount as to provide a molar ratio of the basic catalyst to the fluorine-containing adamantane derivative (I) of about 0.5 to 10, preferably 1 to 5.

To the above-described basic catalyst, a quaternary ammonium salt such as tetramethylammonium chloride or tetraethylammonium bromide may be added as a phase transfer catalyst. The quaternary ammonium salt is used in an amount of about 0.01 to 20 mol %, preferably 0.1 to 10 mol %, based on the basic catalyst.

The reaction is carried out in the absence or presence of a solvent. It is advantageous that the solvent used can dissolve at least 0.5% by mass, preferably at least 5% by mass, of the above-described fluorine-containing adamantane derivative (I). The solvent may be used in such an amount as to provide a concentration of the above-described fluorine-containing adamantane derivative (I) of at least 0.5% by mass, preferably at least 5% by mass. The above-described fluorine-containing adamantane derivative (I) may be present in a suspended state but is preferably in a dissolved state. Specific examples of the solvent include hexane, heptane, toluene, DMF (dimethylformamide), NMP (N-methyl-2-pyrrolidone), DMAc (N,N-dimethylacetaminde), DMSO (dimethylsulfoxide), ethyl acetate, diethyl ether and tetra hydrofuran. These solvents may be used singly or in combination of two or more thereof.

The obtained reaction product may be refined by distillation, crystallization, column separation, etc. The refining method may be suitably selected depending upon the properties of the product and the kind of impurities.

The resin composition according to the present invention comprises the above-described fluorine-containing adamantane derivative (II). As the resin composition according to the present invention, a mixed resin containing the above-described fluorine-containing adamantane derivative (II) and other polymerizable monomer and/or an epoxy resin may also used.

As the "other polymerizable monomer", there may be mentioned, for example, methyl (meth)acrylate, ethyl (meth)acrylate, propyl (meth)acrylate, butyl (meth)acrylate, ethylene glycol (meth)acrylate, 1,3-propane diol di(meth)acrylate, 1,4-butane diol di(meth)acrylate, 1H,1H-perfluoropropyl (meth)acrylate, 1H,1H-perfluorobutyl (meth)acrylate, 1H,1H-perfluorohexyl (meth)acrylate, 1H,1H-perfluorooctyl (meth)acrylate, 1H,1H-perfluorodecyl (meth)acrylate, perfluoro-1-adamantyl (meth)acrylate, perfluoro-2-adamantyl (meth)acrylate, 1H,1H,6H,6H-perfluoro-1,6-hexane diol di(meth)acrylate, 1H,1H,8H,8H-perfluoro-1,8-octane diol di(meth)acrylate, 1H,1H,10H,10H-perfluoro-1,10-decane diol di(meth)acrylate and perfluoro-1,3-adamantane diol di(meth)acrylate. Above all, monomers containing fluorine are preferred. These monomers may be used singly or in combination of two or more thereof.

As the epoxy resin, there may be mentioned, for example, a bisphenol A type epoxy resin, a bisphenol F type epoxy resin (bisphenol A diglycidyl ether, bisphenol AD diglycidyl ether, bisphenol S diglycidyl ether, hydrogenated bisphenol A diglycidyl ether, bisphenol F diglycidyl ether, bisphenol G diglycidyl ether, tetramethylbisphenol A diglycidyl ether, bisphenol AF diglycidyl ether, bisphenol C diglycidyl ether, etc.), a novolak type epoxy resin (a phenol novolak type epoxy resin, a cresol novolak type epoxy resin, etc.), an alicyclic epoxy resin, a nitrogen-containing cyclic epoxy resin (triglycidyl isocyanurate, a hydantoin epoxy resin, etc.), a hydrogenated bisphenol A type epoxy resin, an aliphatic type epoxy resin, a glycidyl ester type epoxy resin, a bisphenol S type epoxy resin, a biphenyl type or dicyclo-ring type epoxy resin (which represents the mainstream of low water absorption cured body type epoxy resins), a naphthalene type epoxy resin, a polyfunctional epoxy resin (trimethylolpropane polyglycidyl ether, glycerol polyglycidyl ether, pentaerythritol polyglycidyl ether, etc.), a fluorine-containing epoxy resin (a bisphenol AF type epoxy resin, etc.) and a glycidyl ester of (meth)acrylic acid. Above all, epoxy resins containing fluorine or epoxy resins free of aromatic rings are preferred. These epoxy resins may be used singly or in combination of two or more thereof.

The epoxy resin may be solid or liquid at ambient temperature. In general, the epoxy resin employed preferably has an average epoxy equivalent of 200 to 2,000. When the epoxy equivalent is 200 or more, a cured product of the epoxy resin composition is not brittle but has suitable strength. When the epoxy equivalent is 2,000 or less, the glass transition point (Tg) of a cured product is not low but is in a suitable range.

In a mixed resin composed of the above-described fluorine-containing adamantane derivative (II) and the "other polymerizable monomer and/or an epoxy resin", the content of the above-described fluorine-containing adamantane derivative (II) is preferably at least 5% by mass, more preferably at least 10% by mass. When the content of the above-described fluorine-containing adamantane derivative (II) is at least 5% by mass, the resin composition of the present invention can provide satisfactory optical characteristics, long-term heat resistance and electrical characteristics.

The resin composition of the present invention can be cured by polymerization using a thermal initiator and/or a photoinitiator. Any thermal initiator may be used as long as it can react with an unsaturated bond-bearing group, an epoxy group or an oxetanyl group upon heating. The thermal initiator may be, for example, an organic peroxide such as benzoyl peroxide, methyl ethyl ketone peroxide, methyl isobutyl peroxide, cumene hydroperoxide or t-butyl hydroperoxide or an azo type initiator such as azobisisobutyronitrile. These initiators may be used singly or in combination of two or more thereof.

Any photoinitiator may be used as long as it can react with an unsaturated bond-bearing group, an epoxy group or an oxetanyl group upon light irradiation. Examples of the photoinitiator include acetophenones, benzophenones, benzyls, benzoin ethers, benzyl ketals, thioxanthones, acylphosphine oxides, acylphosphine esters, aromatic diazonium salts, aromatic sulfonium salts, aromatic iodonium salts, aromatic iodosyl salts, aromatic sulfoxonium salts and metallocene compounds. These initiators may be used singly or in combination of two or more thereof.

The thermal initiator and/or photoinitiator may be preferably used in an amount of 0.01 to 10 parts by mass, more preferably 0.05 to 5 parts by mass, per 100 parts by mass of the above-described fluorine-containing adamantane derivative (II) or the above-described mixed resin (herein after occasionally referred to as resin component). When the content of the polymerization initiator is within the above range, the polymerization can proceed in a suitable manner to form a product having good optical characteristics.

If desired, the resin composition of the present invention can be compounded with a variety of customarily employed additives such as a curing accelerator, an antidegradant, a modifying agent, a silane coupling agent, a defoaming agent, an inorganic powder, a solvent, a leveling agent, a releasing agent, a dye and a pigment.

The curing accelerator is not specifically limited. Examples of the curing accelerator include tertiary amines such as 1,8-diazabicyclo[5.4.0]undecene-7, triethylenediamine and tris(2,4,6-dimethylaminomethyl)phenol, imidazoles such as 2-ethyl-4-methylimidazole and 2-methylimidazole, phosphorus compounds such as triphenylphosphine, tetraphenylphosphonium bromide, tetraphenylphosphonium tetraphenylborate and tetra-n-butylphosphonium o,o-diethylphosphorodithioate, quaternary ammonium salts, organic metal salts and derivatives of these compounds. These accelerators may be used singly or in combination of two or more thereof. Among the above curing accelerators, it is preferable to use a tertiary amine, an imidazole or a phosphorus compound.

The content of the curing accelerator is preferably 0.01 to 8.0 parts by mass, more preferably 0.1 to 3.0 parts by mass, per 100 parts by mass of the above-described resin component. When the content of the curing accelerator falls within the above range, a satisfactory curing accelerating effect can be obtained without causing coloration of the cured product.

As the antidegradant, customarily employed antidegradant may be used. Examples of the antidegradant include phenol compounds, amine compound, organic sulfur compounds and phosphorus compounds.

The phenol compound may be a commercially available product such as Irganox 1010 (manufactured by Ciba Speciality Chemicals, trademark), Irganox 1076 (manufactured by Ciba Speciality Chemicals, trademark), Irganox 1330 (manufactured by Ciba Speciality Chemicals, trademark), Irganox 3114 (manufactured by Ciba Speciality Chemicals, trademark), Irganox 3125 (manufactured by Ciba Speciality Chemicals, trademark), Irganox 3790 (manufactured by Ciba Speciality Chemicals, trademark) BHT, Cyanox 1790 (manufactured by American Cyanamide Corporation, trademark) and Sumilizer GA-80 (manufactured by Sumitomo Chemical Co., Ltd., trademark).

The amine compound may be, for example, Irgastab FS042 (manufactured by Ciba Speciality Chemicals, trademark); GENOX EP (manufactured by Crompton Corporation, trademark, chemical name: dialkyl-N-methylamine oxide); and sterically hindered amines such as ADK STAB LA-52, LA-57, LA-62, LA-63, LA-67, LA-68, LA-77, LA-82, LA-87 and LA-94 (manufactured by Adeka Corporation), Tinuvin123, 144, 440 and 662, Chimassorb 2020, 119 and 944 (manufactured by CSC), Hostavin N30 (manufactured by Hoechst Inc.), Cyasorb UV-3346 and UV-3526 (manufactured by Cytec Inc.), Uval 299 (manufactured by GLC) and Sanduvor PR-31 (manufactured by Clariant Corporation).

The organic sulfur compound may be, for example, DSTP "YOSHITOMI" (manufactured by Yoshitomiyakuhin Co., Ltd., trademark), DLTP "YOSHITOMI" (manufactured by Yoshitomiyakuhin Co., Ltd., trademark), DLTOIB (manufactured by Yoshitomiyakuhin Co., Ltd., trademark), DMTP "YOSHITOMI" (manufactured by Yoshitomiyakuhin Co., Ltd., trademark), Seenox 412S (manufactured by Shipro Kasei Kaisha Ltd., trademark) and Cyanox 1212 (manufactured by American Cyanamide Corporation, trademark).

As the modifying agent, customarily employed modifying agents such as glycols, silicones and alcohols may be used. As the silane coupling agent, customarily employed silane coupling agents such as silane compounds and titanates may be used. As the antifoaming agent, customarily employed antifoaming agents such as silicones may be used. The inorganic powder having a particle size of several nm to 10 μm may be used depending upon the object of use. As the inorganic powder, customarily employed inorganic powder such as glass powder, silica powder, titania, zinc oxide and alumina may be used. A solvent may be used when the epoxy resin is in the form of powder. A solvent may also be used as a diluent for coating. The solvent may be, for example, an aromatic solvent such as toluene and xylene or a ketone solvent such as methyl ethyl ketone, methyl isobutyl ketone and cyclohexanone.

The resin composition of the present invention obtain able by mixing the above resin component, thermal initiator and/or photoinitiator, and desired additives may be poured in a mold (resin mold) or coated to obtain a desired shape, and then cured by heating or irradiation of UV or the like. In the case of thermal curing, the curing temperature is generally about 30 to 200° C., preferably 50 to 150° C. A curing temperature of 30° C. or higher can prevent occurrence of curing failure, while a curing temperature of 200° C. or lower can prevent occurrence of coloration. The curing time is preferably 0.5 to 6 hours, though it varies with the kind of the resin component and polymerization initiator.

In the case of photo curing by irradiation of UV rays, the UV irradiation intensity is arbitrarily determined in view of the kinds of the resin component, polymerization initiator and the thickness of the intended cured product, etc. but is generally about 100 to 5,000 $mJ/cm^2$, preferably 500 to 4,000 $mJ/cm^2$. The UV irradiation may be followed by heating which is preferably carried out at 70 to 200° C. for 0.5 to 12 hours.

The molding method is not specifically limited and may be, for example, injection molding, blow molding or press molding. It is, however, preferred that the molding be carried out in such a manner that the resin composition in the form of pellets is subjected to injection molding using an injection molding machine.

A cured product obtained by curing the resin composition of the present invention has excellent heat resistance and mechanical properties such as surface hardness and is also low in refractive index. The resin composition of the present invention having the excellent properties is suitably used for forming optical semiconductors (LED, etc.) and flat panel displays (organic EL elements, liquid crystals, etc.), as a resin (sealing material or adhesive agent) for electric circuits and optical circuits (optical waveguides), and for forming optoelectric parts such as optical communication lenses and optical films.

Thus, the resin composition of the present invention may be used for forming semiconductor elements or integrated circuits (IC, etc.), discrete semiconductors (diodes, transistors, thermisters), LED (LED lamps, chip LED, light receiving elements, optical semiconductor lenses), sensors (temperature sensors, optical sensors, magnetic sensors), passive components (high frequency devices, resistors, capacitors, etc.), electromechanical components (connectors, switches, relays, etc.), automobile parts (circuit systems, control systems, sensors, lamp seals, etc.), adhesives (optical parts, optical discs, pickup lenses) and surface coatings (optical films).

Further, a cured product obtained by curing the resin composition of the present invention may be suited for use as, for example, a reflection preventing film for liquid crystals and organic EL devices, a coating agent, a liquid crystal spacer, a reflection preventing film for semiconductor resists, a material for nanoinprint, an optical fiber, an optical waveguide, a lens such as a Fresnel lens, a lenticular lens or a microlens array, and a refractive index modulation material for volume holograms.

EXAMPLES

The present invention will be next described in more detail by way of examples but is not limited thereto in any way. In the following examples and comparative examples, cured products obtained were evaluated as follows.
(1) Glass Transition Point
Glass transition point Tg was measured with a differential scanning calorimeter (DSC6200, manufactured by Seiko Instrument, Inc.). A sample (10 mg) was heated in the atmosphere of nitrogen at a heating rate of 10° C./min. The break point observed in the obtained heat flux curve represents Tg.
(2) Durometer Hardness D
Durometer hardness was measured in accordance with JIS K7215 using Durometer D (manufactured by Shore Inc.) as a measuring device.
(3) Bending Test
Bending test was performed in accordance with JIS K7171 using Universal Testing Machine (Model 5582 manufactured by Instron Inc.) as a measuring device.
(4) Refractive Index
Refractive index was measured at 23° C. using Abbe refractometer manufactured by Atago Co., Ltd.

Example 1

Synthesis of
Perfluoro-1,3-bis(2-hydroxyethoxy)adamantane

In a four-necked flask having an inside volume of 500 mL and equipped with a reflux condenser, a stirrer and a thermometer, 30.0 g (71 mmol) of perfluoro-1,3-adamantane diol, 57.5 g (714 mmol) of 2-chloroethanol, 29.6 g (214 mmol) of potassium carbonate and 11.9 g of potassium iodide were placed, to which 100 mL of DMF were added. The flask was placed in an oil bath at 110° C. and the mixture therein was heated and stirred for 2 hours. The reaction liquid was cooled and filtered to remove solid matters. The filtrate was transferred to a separatory funnel, to which 100 mL of ethyl acetate and 100 mL of a 5% by mass aqueous solution of sodium chloride were added. The desired product was extracted into an ethyl acetate layer. The ethyl acetate layer was then washed one time with 100 mL of a 5% by mass aqueous sodium chloride solution and then two times with 100 mL of a 5% by mass aqueous sodium phosphate solution. The ethyl acetate layer was dehydrated with anhydrous magnesium sulfate and the solvent was then removed with an evaporator to leave a crude product. The crude product was allowed to stand quiescently at 0° C. to crystallize the product. With washing with n-hexane, the crystals were collected. The collected crystals were dried until no reduction of the weight was detected, thereby obtaining perfluoro-1,3-bis(2-hydroxyethoxy)adamantane (yield: 74%, purity (by gas chromatography (GC)): 98.9%).

The obtained perfluoro-1,3-bis(2-hydroxyethoxy)adamantane was identified with nuclear magnetic resonance spectroscopy ($^1$H-NMR, $^{13}$C-NMR, $^{19}$F-NMR) and with GC-MS. The nuclear magnetic resonance spectroscopic analysis was performed with JNM-ECA500 (manufactured by JEOL Ltd.) using DMSO-$d_6$ as a solvent, while GC-MS was measured using GCMS-QP2010 (manufactured by Shimadzu Corporation).

$^1$H-NMR (500 MHz): 2.75 (m, 4H), 3.34 (t, 4H), 4.09 (t, 2H)
$^{13}$C-NMR (125 MHz): 60.0, 73.6
$^{19}$F-NMR (465 MHz): −113.1, −117.2, −120.8, −219.9
GC-MS (EI): 448 (M$^+$, 15.4%), 45 (100%), 31 (36.8%)

Example 2

Synthesis of
Perfluoro-1,3-bis(acryloyloxyethoxy)adamantane

In a four-necked flask having an inside volume of 1 L and equipped with a stirrer, a thermometer, a reflux condenser and a dropping funnel, 20.0 g of perfluoro-1,3-bis(2-hydroxyethoxy)adamantane obtained in Example 1 were placed and dissolved in 200 mL of ethyl acetate. To this solution, 13.6 mL of triethylamine were added. Thereafter, 8.0 mL of acrylic chloride was added dropwise from the dropping funnel while maintaining the reaction system at a temperature not exceeding 25° C. After completion of the dropping, the reaction mixture was stirred for 1 hour at room temperature, then mixed with 300 mL of ethyl acetate and 200 mL of a 5% by mass aqueous sodium phosphate solution, and stirred for 10 minutes. The ethyl acetate layer was separated. The remaining aqueous layer was further subjected to extraction with 300 mL of ethyl acetate and an ethyl acetate layer was separated. These two ethyl acetate layers were combined and washed with 200 mL of a 5% by mass aqueous sodium phosphate solution. The washed ethyl acetate layer was separated and dried using anhydrous magnesium sulfate. The solvent was removed by distillation using an evaporator to obtain a crude product. The crude product was dissolved in 500 mL of n-heptane, to which 3.0 g of silica gel were added. The mixture was stirred for 30 minutes to effect decoloration. This was then filtered to remove the silica gel and n-heptane was removed by distillation using an evaporator, thereby obtaining perfluoro-1,3-bis(acryloyloxyethoxy)adamantane (yield: 78%, purity (by GC): 99.0%)

The thus obtained perfluoro-1,3-bis(acryloyloxyethoxy)adamantane was identified with nuclear magnetic resonance spectroscopy ($^1$H-NMR, $^{13}$C-NMR, $^{19}$F-NMR) and with GC-MS. The nuclear magnetic resonance spectroscopic analysis was performed with JNM-ECA500 (manufactured by JEOL Ltd.) using chloroform-d as a solvent, while GC-MS was measured using GCMS-QP2010 (manufactured by Shimadzu Corporation). Perfluoro-1,3-bis(acryloyloxyethoxy)adamantane has a chemical structure shown by the formula below.

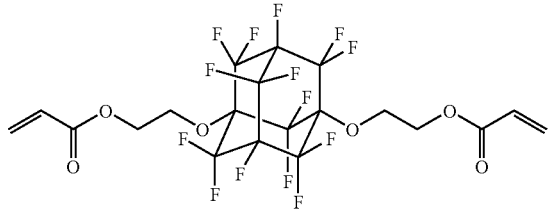

$^1$H-NMR (500 MHz): 4.43 (t, 4H), 4.46 (t, 4H), 5.88 (d, 2H), 6.15 (dd, 2H), 6.44 (d, 2H)
$^{13}$C-NMR (125 MHz): 62.5, 68.9, 127.8, 131.5, 165.7
$^{19}$F-NMR (465 MHz): −113.7, −117.5, −121.0, −220.9
GC-MS (EI): 472 (M$^+$, 12.6%), 99 (6.4%), 55 (100%), 27 (13.3%)

Example 3

To 100 parts by mass of perfluoro-1,3-bis(acryloyloxyethoxy)adamantane obtained in Example 2 were added 2 parts by mass of benzoin isobutyl ether as a photopolymerization initiator. After thorough mixing, the mixture was deaerated under vacuum to obtain a resin composition. The resin composition was poured in a glass cell and irradiated with UV rays using a mercury lamp at a intensity of 1,000 mJ/cm$^2$ to obtain a cured product having a thickness of 1 mm. The cured product was evaluated by the above-described methods to give the results summarized in Table 1.

Comparative Example 1

A curing reaction was performed in the same manner as described in Example 3 except that perfluoro-1,3-bis(acryloyloxyethoxy)adamantane was substituted with 1H,1H,6H,6H-perfluoro-1,6-hexane diol diacrylate having the following formula:

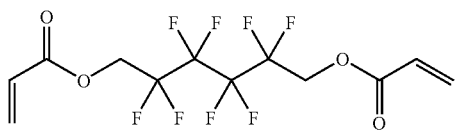

The thus obtained cured product was evaluated by the above-described methods to give the results summarized in Table 1.

TABLE 1

| | Glass transition point (° C.) | Durometer hardness D | Bending strength (MPa) | Bending modulus (MPa) | Refractory index |
|---|---|---|---|---|---|
| Example 3 | 173 | 87 | 71.5 | 2,880 | 1.433 |
| Comparative Example 1 | 121 | 82 | 32.8 | 1,760 | 1.434 |

Example 4

Synthesis of
Perfluoro-1,3-bis(acryloyloxyethoxy)adamantane

In a four-necked flask having an inside volume of 300 mL and equipped with a Dien Stark reflux condenser, a stirrer, a thermometer and a three-way cock, 20.0 g of perfluoro-1,3-bis(2-hydroxyethoxy)adamantane obtained in Example 1, 5.96 g of acrylic acid, 0.39 g of 98% by mass sulfuric acid, 6.0 mg of methoquinone and 100 mL of toluene were placed. The flask was then immersed in an oil bath at 130° C. A small amount of air was streamed through the three-way cock and stirring was started. The reaction was carried out for 8 hours after the start of toluene refluxing. The reaction liquid was cooled to room temperature, to which 100 mL of n-heptane were added. This was transferred to a separatory funnel. The liquid was then washed one time with a 5% by mass aqueous sodium chloride solution, one time with a 3% by mass aqueous disodium hydrogen phosphate solution and, further, one time with a 5% by mass aqueous sodium chloride solution. The washed organic layer was separated and dried using anhydrous magnesium sulfate. The anhydrous magnesium sulfate was separated by filtration, to which 3.0 g of silica gel were added. The mixture was stirred for 30 minutes to effect decoloration. This was then filtered to remove the silica gel and the solvent was removed by distillation using an evaporator, thereby obtaining perfluoro-1,3-bis(acryloyloxyethoxy)adamantane (yield: 81%, purity (by GC): 98%). The nuclear magnetic resonance spectra ($^1$H-NMR, $^{13}$C-NMR and $^{19}$F-NMR) and GC-MS spectrum of the obtained perfluoro-1,3-bis(acryloyloxyethoxy)-adamantane were found to be the same as those of the adamantane product obtained in Example 2.

Example 5

Synthesis of
Perfluoro-1,3-bis(glycidyloxyethoxy)adamantane

In a four-necked flask having an inside volume of 500 mL and equipped with a reflux condenser, a stirrer and a thermometer, 35.0 g of perfluoro-1,3-bis(2-hydroxyethoxy)adamantane obtained in Example 1, 102.0 g of epichlorohydrin, 6.89 g of sodium hydroxide and 3.50 g of tetraethylammonium bromide were placed. The flask was then immersed in a water bath at 25° C. and the mixture therein was stirred for 20 hours. The reaction solution was dissolved in 450 mL of toluene and transferred to a separatory funnel. The liquid was then washed one time with 450 mL of pure water, one time with 450 mL of a 0.1 mol/L aqueous hydrochloric acid and, further, one time with 450 mL of pure water. The washed organic layer was separated and dried using anhydrous magnesium sulfate. The anhydrous magnesium sulfate was separated by filtration and the solvent was removed by distillation using an evaporator, thereby obtaining perfluoro-1,3-bis(glycidyloxyethoxy)adamantane (yield: 85%, purity (by GC): 96%).

The thus obtained perfluoro-1,3-bis(glycidyloxyethoxy)adamantane was identified with nuclear magnetic resonance spectroscopy ($^1$H-NMR, $^{13}$C-NMR and $^{19}$F-NMR) and with GC-MS. The nuclear magnetic resonance spectroscopic analysis was performed with JNM-ECA500 (manufactured by JEOL Ltd.) using chloroform-d as a solvent, while GC-MS was measured using GCMS-QP2010 (manufactured by Shimadzu Corporation). Perfluoro-1,3-bis(glycidyloxyethoxy)adamantane has a chemical structure shown by the formula below.

$^1$H-NMR (500 MHz): 2.63 (dd, 2H), 2.79 (t, 2H), 3.15 (m, 2H), 3.48 (dd, 2H), 3.79 (m, 4H), 3.86 (dd, 2H), 4.36 (t, 4H)

$^{13}$C-NMR (125 MHz): 44.0, 50.9, 69.8, 70.9, 72.0

$^{19}$F-NMR (465 MHz): −113.5, −117.4, −121.1, −220.8

GC-MS (EI): 29 (100%), 43 (32.2%), 45 (68.6%), 57 (93.6%), 87 (30.8%), 100 (46.4%), 473 (14.3%), 491 (5.1%),

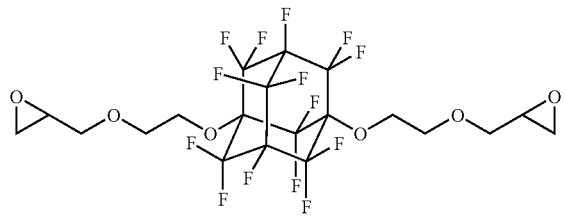

INDUSTRIAL APPLICABILITY

The polymerizable group-containing and fluorine-containing adamantane derivative according to the present invention and the resin composition containing such a derivative have good heat resistance and good mechanical properties such as surface hardness and can give a cured product having a low refractive index. Therefore, they may be suitably used for forming a low refractive index layer for a reflection preventing film, an optical fiber, an optical waveguide and various types of lenses. Further, when they are used for forming a low refractive index layer of a reflection preventing film for a display such as an organic EL element or a liquid crystal, it is possible to improve the surface hardness of the reflection preventing film.

Further, the polymerizable group-containing and fluorine-containing adamantane derivative of the present invention, which can give a cured product having a low refractive index and good heat resistance, may be suited for use as an optical fiber or an optical waveguide material.

In addition, the polymerizable group-containing and fluorine-containing adamantane derivative of the present invention, which can give a cured product having a low refractive index and good heat resistance, may be suitably used as a reflection preventing film material of a reflection preventing film for a semiconductor resist and as a refractive index modulation material for a volume hologram.

The invention claimed is:

1. A fluorine-containing adamantane derivative represented by the following general formula (I):

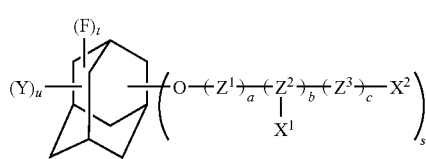

wherein
$Z^1$, $Z^2$ and $Z^3$ represent the groups represented by the following formulas:

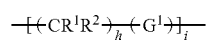

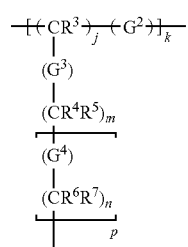

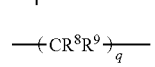

where
$R^1$ to $R^9$ each independently represent a hydrogen atom, a halogen atom or an aliphatic hydrocarbon group which may comprise a heteroatom or heteroatoms,
$G^1$ to $G^4$ each independently represent a single bond or a heteroatom,
h, i, j, k, n, p and q each represent an integer of 1 or more,
m represents an integer of 0 or more,
a, b and c each represents an integer of 0 or more with the proviso that $a+b+c \geq 1$, $X^1$ and $X^2$ each independently represent a hydroxyl group or an amino group,
Y represents a hydrogen atom, a hydrocarbon group, a halogenated hydrocarbon group, a cyclic hydrocarbon group, a halogenated cyclic hydrocarbon group, a hydroxyl group or a carboxyl group, or two Y's may be taken together to represent a =O group,
s represents an integer of 2,
t represents an integer of 14, and
u represents an integer of 0.

2. A polymerizable group-containing and fluorine-containing adamantane derivative represented by the following general formula (II):

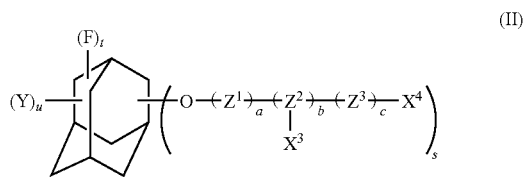

wherein
$Z^1$, $Z^2$ and $Z^3$ represent the groups represented by the following formulas:

where
$R^1$ to $R^9$ each independently represent a hydrogen atom, a halogen atom or an aliphatic hydrocarbon group which may comprise a heteroatom or heteroatoms,
$G^1$ to $G^4$ each independently represent a single bond or a heteroatom,
h, i, j, k, n, p and q each represent an integer of 1 or more,
m represents an integer of 0 or more,
a, b and c each represents an integer of 0 or more with the proviso that $a+b+c \geq 1$,
$X^3$ and $X^4$ each independently represent a polymerizable group represented by any of the following general formulas (III) to (VI):

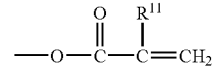

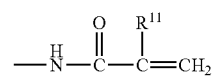

-continued

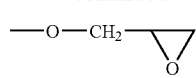           (V)

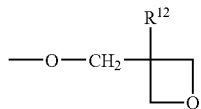           (VI)

where
$R^{11}$ represents a hydrogen atom, a methyl group or a trifluoromethyl group,
$R^{12}$ represents a $C_1$ to $C_5$ hydrocarbon group,
Y represents a hydrogen atom, a hydrocarbon group, a halogenated hydrocarbon group, a cyclic hydrocarbon group, a halogenated cyclic hydrocarbon group, a hydroxyl group, a carboxyl group or two Y's may be taken together to represent a =O group,
s represents an integer of 2,
t represents an integer of 14, and
u represents an integer of 0.

3. A process for producing a polymerizable group-containing and fluorine-containing adamantane derivative represented by the general formula (II) shown below, comprising reacting a fluorine containing adamantane derivative represented by the general formula (I) shown below with a compound comprising a polymerizable group:

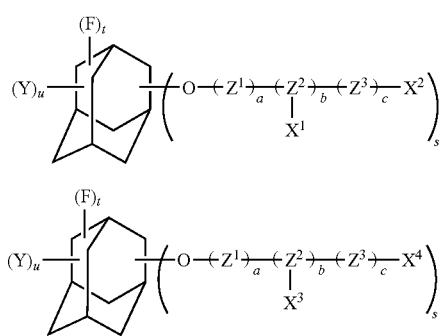

wherein
$Z^1$, $Z^2$ and $Z^3$ represent the groups represented by the following formulas:

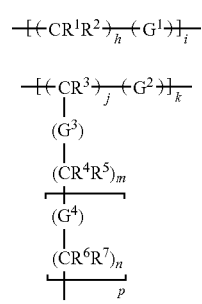

where
$R^1$ to $R^9$ each independently represent a hydrogen atom, a halogen atom or an aliphatic hydrocarbon group which may comprise a heteroatom or heteroatoms,
$G^1$ to $G^4$ each independently represent a single bond or a heteroatom,
h, i, j, k, n, p and q each represent an integer of 1 or more,
m represents an integer of 0 or more,
a, b and c each represents an integer of 0 or more with the proviso that $a+b+c \geq 1$,
$X^1$ and $X^2$ each independently represent a hydroxyl group or an amino group,
Y represents a hydrogen atom, a hydrocarbon group, a halogenated hydrocarbon group, a cyclic hydrocarbon group, a halogenated cyclic hydrocarbon group, a hydroxyl group, a carboxyl group or two Y's may be taken together to represent a =O group,
$X^3$ and $X^4$ each independently represent a polymerizable group represented by any of the following general formulas (III) to (VI):

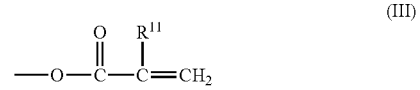           (III)

           (IV)

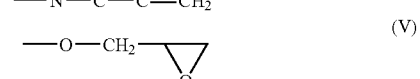           (V)

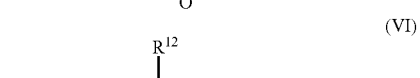           (VI)

where
$R^{11}$ represents a hydrogen atom, a methyl group or a trifluoromethyl group,
$R^{12}$ represents a $C_1$ to $C_5$ hydrocarbon group,
s represents an integer of 2,
t represents an integer of 14, and
u represents an integer of 0.

4. A resin composition comprising the polymerizable group-containing and fluorine-containing adamantane derivative represented by the general formula (II) according to claim 2.

5. The fluorine-containing adamantane derivative according to claim 1, which is perfluoro-1,3-bis(2-hydroxyethoxy)adamantane.

6. The polymerizable group-containing and fluorine-containing adamantane derivative according to claim 2, which is perfluoro-1,3-bis(acryloyloxyethoxy)adamantane.

7. The polymerizable group-containing and fluorine-containing adamantane derivative according to claim 2, which is perfluoro-1,3-bis(glycidyloxyethoxy)adamantane.

* * * * *